United States Patent
Denis et al.

(10) Patent No.: US 11,084,797 B2
(45) Date of Patent: Aug. 10, 2021

(54) PROCESS FOR PRODUCING 5-HYDROXYMETHYLFURFURAL IN THE PRESENCE OF AN INORGANIC DEHYDRATION AND A CHLORIDE SOURCE

(71) Applicant: IFP Energies nouvelles, Rueil-Malmaison (FR)

(72) Inventors: Justine Denis, Feyzin (FR); Marc Jacquin, Lyons (FR); Damien Delcroix, St Maurice L Exil (FR)

(73) Assignee: IFP Energies nouvelles, Rueil-Malmaison (FR)

( * ) Notice: Subject to any disclaimer, the term of this patent is extended or adjusted under 35 U.S.C. 154(b) by 0 days.

(21) Appl. No.: 16/651,381

(22) PCT Filed: Sep. 25, 2018

(86) PCT No.: PCT/EP2018/075964
§ 371 (c)(1),
(2) Date: Mar. 27, 2020

(87) PCT Pub. No.: WO2019/063546
PCT Pub. Date: Apr. 4, 2019

(65) Prior Publication Data
US 2020/0299250 A1    Sep. 24, 2020

(30) Foreign Application Priority Data
Sep. 28, 2017  (FR) ........................................ 1759025

(51) Int. Cl.
*C07D 307/48*    (2006.01)
(52) U.S. Cl.
CPC .................. *C07D 307/48* (2013.01)

(58) Field of Classification Search
CPC .................................................... C07D 307/48
See application file for complete search history.

(56) References Cited

U.S. PATENT DOCUMENTS

| 8,680,264 | B2 | 3/2014 | Binder et al. |
| 2008/0033187 | A1 | 2/2008 | Zhao et al. |
| 2010/0004437 | A1* | 1/2010 | Binder ................. C07D 307/28 536/124 |
| 2014/0235881 | A1 | 8/2014 | Cho et al. |
| 2014/0357878 | A1 | 12/2014 | Zhang et al. |
| 2015/0045576 | A1 | 2/2015 | Benecke et al. |

FOREIGN PATENT DOCUMENTS

WO    09155297 A1   12/2009

OTHER PUBLICATIONS

Tian Guo et al: "Tin-catalyzed efficient conversion of carbohydrates for the production of 5-hydroxymethylfurfural in the presence of quaternary ammonium salts", Carbohydrate Research, Pergamon, GB, vol. 370, Jan. 30, 2013 (Jan. 30, 2013), pp. 33-37, XP028991035, ISSN: 0008-6215, DOI: 10.1016/J.CARRES.2013.01.012.
International Search report PCT/EP2018/075964 ( pp. 1-3) dated Oct. 22, 2018.

* cited by examiner

*Primary Examiner* — Timothy R Rozof
(74) *Attorney, Agent, or Firm* — Millen, White, Zelano and Branigan, P.C.

(57) ABSTRACT

The invention relates to a process for converting a feedstock comprising at least one sugar into 5-hydroxymethylfurfural, wherein said feed is brought into contact with one or more inorganic dehydration catalysts and one or more chloride sources in the presence of at least one aprotic polar solvent alone or as a mixture, at a temperature of between 30° C. and 200° C., and at a pressure of between 0.1 MPa and 10 MPa.

20 Claims, No Drawings

PROCESS FOR PRODUCING 5-HYDROXYMETHYLFURFURAL IN THE PRESENCE OF AN INORGANIC DEHYDRATION AND A CHLORIDE SOURCE

TECHNICAL FIELD OF THE INVENTION

The invention relates to a process for converting sugars and in particular hexoses into 5-hydroxymethylfurfural in the presence of inorganic dehydration catalysts and of a chloride source in the presence of at least one aprotic polar solvent.

PRIOR ART 5-hydroxymethylfurfural (5-HMF) is a compound derived from biomass which can be exploited in many fields, notably as a precursor of active ingredients in pharmacy, agrochemistry or specialty chemistry. Its advantage in recent years has been its use as a precursor of furanedicarboxylic acid (FDCA) which is used as a substitute for terephthalic acid as a monomer for the production of polyester fibers or convenience plastics.

The production of 5-HMF by dehydration of hexoses has been known for many years and has been the subject of a large number of research works. On the one hand, the dehydration of glucose or fructose to 5-HMF is described in the presence of aprotic polar solvent, for example dimethyl sulfoxide DMSO or N-methylpyrrolidone NMP, in the presence of a heterogeneous acid catalyst, that is to say supported catalysts insoluble in the reaction medium, such as sulfonic silicas described by Bao et al., Catal. Common. 2008, 9, 1383, with performances corresponding to 5-HMF yields of approximately 70%. On the other hand, the dehydration of glucose or fructose to 5-HMF is described, for example in patent applications U.S. 2014/0235881, U.S. 2014/0357878 and U.S. 2015/0045576, in the presence of aprotic polar solvent, for example water or ethanol, in the presence of heterogeneous or homogeneous acid catalysts, that is to say for the latter that they are soluble in the reaction medium, with the formation of by-products of the carboxylic acid, ester and ether family, such as levulinic acid and its esters, formic acid and its esters and also the alkoxylated derivatives of 5-HMF such as 5-ethoxymethylfurfural. The obtaining of these products is detrimental to the yield, and imposes additional costly separation and purification steps reducing the economic profitability of the process.

There is therefore a need to develop new processes for the selective transformation of sugars into 5-HMF, making it possible to obtain better yields by limiting the formation of unwanted by-products.

Surprisingly, the applicant has demonstrated that bringing sugars into contact with one or more inorganic dehydration catalysts and one or more chloride sources in the presence of at least one aprotic polar solvent makes it possible to significantly increase the 5-HMF yields by limiting the formation of unwanted by-products, compared to inorganic dehydration catalysts used without a chloride source.

The invention therefore relates to a process for producing 5-hydroxymethylfurfural from sugars using an inorganic dehydration catalyst in combination with a chloride source in the presence of at least one aprotic polar solvent.

SUBJECT OF THE INVENTION

It is therefore an object of the present invention to provide a new process for converting a feedstock comprising at least one sugar into 5-hydroxymethylfurfural, wherein said feedstock is brought into contact with one or more inorganic acid catalysts and one or more chloride sources in the presence of at least one aprotic polar solvent alone or as a mixture, at a temperature of between 30° C. and 200° C., and at a pressure of between 0.1 MPa and 10 MPa.

One advantage of the present invention is to provide a process for converting sugars into 5-hydroxymethylfurfural (5-HMF) which makes it possible to increase the 5-HMF yield and to limit the formation of unwanted by-products such as the products of the carboxylic acid, ester, ether and humin family. Humins are secondary products of condensation in an acid medium, such as polyfurans.

DEFINITIONS AND ABBREVIATIONS

It is specified, throughout this description, that the expression "of between . . . and . . . " should be understood as including the limits mentioned.

The term "inorganic acid dehydration catalyst" is intended to mean any catalyst chosen from Brønsted acids and Lewis acids, which may be homogeneous or heterogeneous, capable of inducing dehydration reactions such as those of sugars to 5-hydroxymethylfurfural.

The term "chloride source" is intended to mean any compound of general formula $Q_yCl_z$ wherein Q can represent a hydrogen, an alkali or alkaline-earth metal chosen from groups 1 and 2 of the periodic table or an organic cation chosen from the ammonium, phosphonium and guanidinium family.

The term "inorganic catalyst" is intended to mean a catalyst wherein the acid function responsible for the catalytic dehydration activity is not bonded to a hydrocarbon-based chain by a covalent bond.

The term "homogeneous catalyst" is intended to mean a catalyst which is soluble in the reaction medium.

The term "heterogeneous catalyst" is intended to mean a catalyst which is insoluble in the reaction medium.

The term "inorganic Brønsted acid catalyst" is intended to mean a Brønsted acid catalyst that does not contain carbon atoms.

The term "inorganic Lewis acid catalyst" is understood to mean a Lewis acid catalyst containing an atom from the family of metals or lanthanides.

The term "alkyl group" is intended to mean a linear or branched, and noncyclic, cyclic or polycyclic, saturated hydrocarbon-based chain containing between 1 and 20 carbon atoms.

The term "alkenyls" is intended to mean a hydrocarbon-chain containing between 1 and 20 atoms, comprising at least one, linear or branched, cyclic or non-cyclic unsaturation.

The term "aryl group" is intended to mean a mono or polycyclic, fused or non-fused aromatic group comprising between 5 and 30 carbons.

The term "heteroaryl group" is intended to mean an aromatic group comprising between 4 and 30 carbon atoms and at least, within at least one aromatic nucleus, one heteroatom chosen from oxygen, sulfur and nitrogen.

The term "alkyl halide" is intended to mean an alkyl substituted with at least one halogen atom chosen from fluorine, chlorine, bromine or iodine.

The term "anionic halide entity" is intended to mean a halogen atom chosen from fluorine, chlorine, bromine or iodine.

The term "aprotic solvent" is intended to mean a molecule acting as a solvent and all the hydrogens of which are borne by carbon atoms.

The term "polar solvent" is intended to mean a molecule acting as a solvent, the dipole moment μ of which, expressed in Debye, has a numerical value greater than or equal to 2.00 measured at 25° C.

The term "aprotic polar solvent" is therefore intended to mean a molecule acting as a solvent, all the hydrogens of which are borne by carbon atoms and the dipole moment μ of which, expressed in Debye, has a numerical value greater than or equal to 2.00 measured at 25° C.

BRIEF DESCRIPTION OF THE INVENTION

Advantageously, the process according to the invention is a process for converting a feedstock comprising at least one sugar into 5-hydroxymethylfurfural, wherein said feedstock is brought into contact with at least one inorganic dehydration catalyst and at least one chloride source of general formula (III) $Q_yCl_z$ in the presence of at least one aprotic polar solvent, at a temperature of between 30° C. and 200° C. and a pressure of between 0.1 and 10 MPa, wherein Q is chosen from hydrogen, an alkali or alkaline-earth metal chosen from groups 1 and 2 of the periodic table or an organic cation chosen from the ammonium, phosphonium and guanidinium family.

y is between 1 and 10, z is between 1 and 10.

DETAILED DESCRIPTION OF THE INVENTION

Within the meaning of the present invention, the various embodiments presented can be used alone or in combination with one another, without any limit to the combinations.

The Feedstock

The feedstock treated in the process according to the invention is a feedstock comprising at least one sugar, preferably chosen from oligosaccharides and monosaccharides, alone or as a mixture.

The term "monosaccharide" denotes the compounds corresponding to the general formula (Ia) $C_6(H_2O)_6$ or $C_6H_{12}O_6$. Preferably, the monosaccharides are chosen from glucose, mannose and fructose, alone or as a mixture.

The term "oligosaccharide" denotes the compounds having the empirical formula (Ib) $C_{6n}H_{10n-2}O_{5n+1}$ wherein n is an integer between 1 and 10, the monosaccharide units making up said oligosaccharide being identical or different, and the compounds having the empirical formula (Ic) $(C_{6m}H_{10m+2}O_{5m+1})(C_{5p}H_{8p+2}O_{4p+1})$ wherein m and p are independently integers between 1 and 10, the monosaccharide units making up said oligosaccharide being identical or different.

The oligosaccharides are preferably chosen from hexose oligomers or oligomers of pentoses and hexoses, preferably from hexose oligomers. They can be obtained by partial hydrolysis of polysaccharides from renewable resources such as starch, inulin, cellulose or hemicellulose, optionally from lignocellulosic biomass. Steam explosion of lignocellulosic biomass is a process of partial hydrolysis of the cellulose and hemicellulose contained in lignocellulosic biomass, producing a stream of oligo- and monosaccharides.

Preferably, the oligosaccharides are chosen from sucrose, lactose, maltose, isomaltose, inulobiose, melibiose, gentiobiose, trehalose, cellobiose, cellotriose, cellotetraose and oligosaccharides resulting from the hydrolysis of said polysaccharides resulting from the hydrolysis of starch, inulin, cellulose or hemicellulose, alone or as a mixture.

Preferably, the feedstock is chosen from sucrose, fructose and glucose, alone or as a mixture. Very preferably, said feedstock is chosen from fructose and glucose, alone or as a mixture.

The Dehydration Catalysts

In accordance with the invention, said feedstock is brought into contact in the process with at least one inorganic dehydration catalyst chosen from homogeneous inorganic Brønsted acids and homogeneous or heterogeneous inorganic Lewis acids, capable of catalyzing the dehydration of the feedstock to 5-hydroxymethylfurfural.

Preferably, the inorganic dehydration catalyst is chosen from the following homogeneous inorganic Brønsted acids: HF, HCl, HBr, HI, $H_2SO_3$, $H_2SO_4$, $H_3PO_2$, $H_3PO_4$, $HNO_2$, $HNO_3$, $H_2WO_4$, $H_4SW_{12}O_{40}$, $H_3PW_{12}O_{40}$, $(NH_4)_6(W_{12}O_{40}).xH_2O$, $H_4SiMo_{12}O_{40}$, $H_3PMo_{12}O_{40}$, $(NH_4)_6Mo_7O_{24}.xH_2O$, $H_2MoO_4$, $HReO_4$, $H_2CrO_4$, $H_2SnO_3$, $H_4SiO_4$, $H_3BO_3$, $HClO_4$, $HBF_4$, $HSbF_5$, $HPF_6$, $H_2FO_3P$, $ClSO_3H$, $FSO_3H$, $HN(SO_2F)_2$ and $HIO_3$. Preferably, the inorganic Brønsted acids are chosen from the following list: $H_2SO_4$, $H_3PO_4$, $HNO_3$.

Preferably, the inorganic dehydration catalyst is chosen from homogeneous inorganic Lewis acids corresponding to general formula (II) $M_oX_p$ which may or may not be solvated, wherein M is an atom chosen from the atoms from groups 3 to 16, preferably 6 to 13, of the periodic table, lanthanides included, and preferably from B, Al, Fe, Zn, Sn, Cr, Ce and Er, and preferably from Al, Sn and Cr, o is an integer between 1 and 10, preferably between 1 and 5, and preferably between 1 and 2, p is an integer between 1 and 10, preferably between 1 and 5, and preferably between 1 and 3, and X is an anion chosen from hydroxides, halides, nitrates, carboxylates, halocarboxylates, acetylacetonates, alkoxides, phenolates, which are substituted or unsubstituted, sulfates, alkyl sulfates, phosphates, alkyl phosphates, halosulfonates, alkyl sulfonates, perhaloalkyl sulfonates, bis(perhaloalkylsulfonyl)amides, arenesulfonates, which are unsubstituted or substituted with halogen or haloalkyl groups, preferably X is chosen from halides, sulfates, alkyl sulfonates, perhaloalkyl sulfonates which are unsubstituted or substituted with halogen or haloalkyl groups, it being possible for said anions X to be identical or different in the case where o is greater than 1.

Very preferably, the homogeneous inorganic Lewis acids are chosen from $BF_3$, $AlCl_3$, $Al(OTf)_3$, $FeCl_3$, $ZnCl_2$, $SnCl_2$, $CrCl_3$, $CeCl_3$ and $ErCl_3$. Very preferably, the homogeneous inorganic Lewis acid is $AlCl_3$.

The heterogeneous inorganic Lewis acids are chosen from simple or mixed oxides of the compounds chosen from silicon, aluminum, zirconium, titanium, niobium, tungsten, which are undoped or doped with an element chosen from tin, tungsten and hafnium, and from metal phosphates, said metals being chosen from niobium, zirconium, tantalum, tin and titanium. Preferably, the heterogeneous Lewis acids are chosen from zirconium oxides, titanium oxides, mixed oxides of aluminum and silicon doped with tin, such as the Sn-β zeolite or the mesostructured silica Sn-MCM-41, tin phosphates and titanium phosphates.

The Chloride Sources

In accordance with the invention, in combination with the inorganic dehydration catalyst(s) defined above, said feedstock is brought into contact in the process according to the invention with one or more chloride sources of general formula (III) $Q_yCl_z$ wherein Q is chosen from hydrogen, an alkali or alkaline-earth metal chosen from groups 1 and 2 of the periodic table or an organic cation chosen from the ammonium, phosphonium and guanidinium family.

y is between 1 and 10, preferably between 1 and 5 and preferably between 1 and 2;

z is between 1 and 10, preferably between 1 and 5 and preferably between 1 and 2.

Preferably, Q is a cation chosen from H, Li, Na, K, Rb, Cs, Fr, Mg, Ca, Sr and Ba, more preferably from H, Li, Na, K, Cs, Mg, Ca and Ba, and very preferably from Li, Na, K, Mg and Ca.

In the case where Q is an organic cation chosen from the ammonium family, the chloride source is chosen from the compounds corresponding to general formula (IIIa)

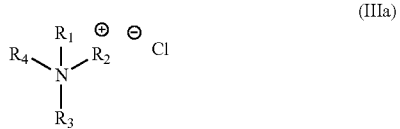

wherein $R_1$ to $R_4$, which may be identical or different, are independently chosen from alkyl groups comprising from 1 to 20 carbons, optionally substituted with at least one group chosen from the following list: aldehyde —C(O)H, ketone —C(O)R", carboxylic acid —COOH, ester —COOR", hydroxymethyl —CH$_2$OH, ether —CH$_2$OR", halogenated —CH$_2$X with X=Cl, Br, I, aryl groups comprising from 5 to 20 carbons, optionally substituted with at least one group chosen from the following list: aldehyde —C(O)H, ketone —C(O)R", carboxylic acid —COOH, ester —COOR", hydroxymethyl —CH$_2$OH, ether —CH$_2$OR", halogenated —CH$_2$X with X=Cl, Br, I, wherein R" is an alkyl group comprising from 1 to 15 carbon atoms, preferably from 1 to 10 and preferably from 1 to 6.

Preferably, the groups $R_1$ to $R_4$, which may be identical or different, preferably linear, are independently chosen from alkyl groups preferably comprising between 1 and 15 carbon atoms, preferably between 1 and 10, preferably between 1 and 8, preferably between 1 and 6, and preferably from 1 to 4 carbon atoms.

Preferably, said groups $R_1$ to $R_4$ are chosen from alkyls substituted with at least one group chosen from —OH and —COOH.

Preferably, said groups $R_1$ to $R_4$ are independently chosen from n-butyl, methyl, n-octyl, hydroxymethyl, hydroxyethyl, hydroxypropyl, hydroxybutyl, —CH$_2$COOH, —CH$_2$CH$_2$COOH and CH$_2$CH$_2$CH$_2$COOH groups, preferably from the methyl, hydroxyethyl and —CH$_2$CH$_2$COOH groups.

Very preferably, the ammoniums are chosen from trioctylmethylammonium chloride ([(CH$_3$(CH$_2$)$_7$)$_3$(CH$_3$)N$^+$Cl$^-$]), choline chloride ([((CH$_3$)$_3$NCH$_2$CH$_2$OH)$^+$Cl$^-$]), betaine chloride ([((CH$_3$)$_3$NCH$_2$COOH)$^+$Cl$^-$]), and tetramethylammonium chloride ([(CH$_3$)$_4$N$^+$Cl$^-$]).

In the case where Q is an organic cation chosen from the guanidinium chloride family, the chloride source is chosen from the compounds corresponding to general formula (IIIb)

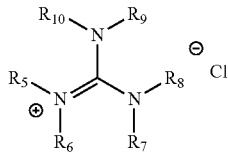

wherein the groups $R_5$ to $R_{10}$, which may be identical or different, are independently chosen from hydrogen, and alkyl and aryl groups.

Preferably, the groups $R_5$ to $R_{10}$, which may be identical or different, are chosen from hydrogen, alkyl groups, which are preferably linear, comprising from 1 to 15 carbon atoms, preferably from 1 to 10 carbon atoms and preferably from 1 to 6 carbon atoms.

Very preferably, the groups $R_5$ to $R_{10}$, which may be identical or different, are independently chosen from hydrogen, and methyl, ethyl, propyl and butyl groups.

Preferably, the groups $R_5$ to $R_{10}$, which may be identical or different, are chosen from aryl groups comprising between 5 and 20 carbon atoms.

Preferably, in the case where Q is an organic cation chosen from the guanidinium family, the chloride source is guanidinium chloride and hexamethylguanidinium chloride.

In the case where Q is an organic cation chosen from the phosphonium family, the chloride source is chosen from the compounds corresponding to general formula (IIIc)

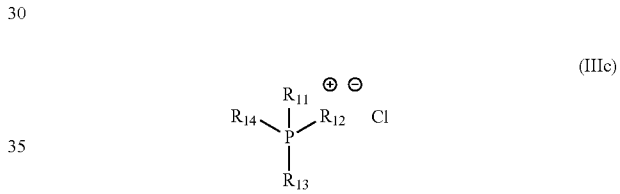

wherein $R_{11}$ to $R_{14}$, which may be identical or different, are independently chosen from alkyl groups, aryl groups and phosphazene groups of general formula (IIId)

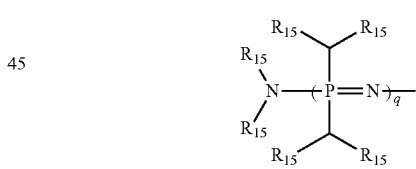

wherein $R_{15}$ is an alkyl group comprising from 1 to 10 carbon atoms, preferably from 1 to 5, and q is an integer between 0 and 10.

Preferably, $R_{11}$ to $R_{14}$, which may be identical or different, are chosen from alkyl groups, which are preferably linear, comprising from 1 to 15 carbon atoms, preferably between 1 and 10 carbon atoms and preferably from 1 to 6 carbon atoms.

Preferably, the groups $R_{11}$ to $R_{14}$, which may be identical or different, are chosen from a phosphazene group characterized by $R_{15}$=methyl and q=1, a methyl, ethyl, n-propyl, n-butyl group.

Preferably, in the case where Q is an organic cation chosen from the phosphonium family, the chloride source is tetraethylphosphonium chloride and tetra(n-butyl)phosphonium chloride.

Advantageously, the use of a chloride source in a conversion process in accordance with the invention makes it possible to limit the formation of unwanted by-products such as the products of the carboxylic acid, ester, ether and humin family.

Conversion Process

In accordance with the invention, the process for converting the feedstock comprising at least one sugar is carried out in a reaction chamber in the presence of at least one solvent, said solvent being an aprotic polar solvent or a mixture of aprotic polar solvents, at a temperature of between 30° C. and 200° C., and at a pressure between 0.1 MPa and 10 MPa.

The process can be carried out in a reaction chamber comprising at least one aprotic polar solvent and wherein said feedstock is placed in the presence of one or more dehydration catalysts and one or more chloride sources.

In accordance with the invention, the process is performed in the presence of at least one solvent, said solvent being an aprotic polar solvent or a mixture of aprotic polar solvents.

The aprotic polar solvents are advantageously chosen from all the aprotic polar solvents of which the dipole moment expressed in Debye (D) is greater than or equal to 2.00. Preferably, the aprotic polar solvents are chosen from pyridine (2.37), butan-2-one (5.22), acetone (2.86), acetic anhydride (2.82), N,N,N',N'-tetramethylurea (3.48), benzonitrile (4.05), acetonitrile (3.45), methyl ethyl ketone (2.76), propionitrile (3.57), hexamethylphosphoramide (5.55), nitrobenzene (4.02), nitromethane (3.57), N,N-dimethylformamide (3.87), N,N-dimethylacetamide (3.72), sulfolane (4.80), N-methylpyrrolidone (4.09), dimethyl sulfoxide (3.90), propylene carbonate (4.94) and γ-valerolactone (4.71) alone or as a mixture.

Preferably, the aprotic polar solvents are advantageously chosen from acetone, N,N-dimethylformamide, N,N-dimethylacetamide, sulfolane, N-methylpyrrolidone, dimethyl sulfoxide, propylene carbonate and γ-valerolactone alone or as mixture.

Preferably, the aprotic polar solvents are advantageously chosen from N,N-dimethylacetamide, N-methylpyrrolidone, dimethyl sulfoxide and γ-valerolactone alone or as a mixture.

Preferably, said process according to the invention is performed at a temperature of between 40° C. and 175° C., preferably between 50 and 120° C., preferably between 60 and 100° C. and very preferably between 65 and 90° C., and at a pressure between 0.1 MPa and 8 MPa and preferably between 0.1 and 5 MPa.

Generally the process can be performed according to different embodiments. Thus, the process can advantageously be carried out batchwise or continuously. The process can be carried out in a closed reaction chamber or in a semi-open reactor.

The inorganic dehydration catalyst(s) are introduced into the reaction chamber in an amount corresponding to a feedstock/catalyst(s) weight ratio of between 1 and 1000, preferably between 1 and 500, preferably between 1 and 200, preferably between 1 and 150.

The chloride source(s) are introduced into the reaction chamber in an amount corresponding to a feedstock/chloride source(s) weight ratio of between 1 and 1000, preferably between 1 and 800, preferably between 1 and 500, preferably between 1 and 400.

The feedstock is introduced into the process in an amount corresponding to a solvent/feedstock weight ratio of between 0.1 and 200, preferably between 0.3 and 100 and more preferentially between 1 and 50.

If a continuous process is chosen, the weight hourly space velocity (flow rate of feedstock by weight/weight of catalyst(s)) is between 0.01 and 10 $h^{-1}$, preferably between 0.02 and 5 $h^{-1}$, preferably between 0.03 and 2 $h^{-1}$.

At the end of the reaction, the dehydration catalyst and the chloride source can be easily recovered by precipitation, distillation, extraction or washing.

The Products Obtained and the Method of Analysis Thereof

The product selectively obtained my means of the conversion process according to the invention is 5-hydroxymethylfurfural (5-HMF).

At the end of the reaction carried out in the process according to the invention, the reaction medium is analyzed by gas chromatography (GC) to determine the 5-HMF content in the presence of an internal standard, and by ion chromatography to determine the conversion of the feedstock in the presence of an external standard and to quantify the unwanted products such as levulinic acid and formic acid. The humins are quantified by difference in carbon balance with the carbon initially introduced.

EXAMPLES

The examples below illustrate the invention without limiting the scope thereof.

In the examples below, the glucose and fructose used as feedstock are commercially available and used without further purification.

The aluminum chloride denoted $AlCl_3$, the lithium chloride denoted LiCl, the potassium chloride denoted KCl, the lithium bromide denoted LiBr, the lithium fluoride denoted LiF, the choline chloride denoted ChCl, the betaine chloride denoted BetC, the tetramethylammonium chloride denoted TMACl, and the dimethyl sulfoxide, noted DMSO, in the examples below are commercially available and used without additional purification.

The dimethyl sulfoxide, denoted DMSO in the examples, used as aprotic polar solvent, is commercially available and used without further purification.

For examples 1 to 8 of conversion of sugars into 5-HMF, the molar yield of 5-HMF is calculated by the ratio between the number of moles of 5-HMF obtained and the number of moles of sugar feedstock used.

The processes of examples from 1 to 10 are carried out at 0.1 MPa.

Example 1

Fructose Conversion Using Aluminum Chloride Alone in DMSO (Not in Accordance with the Invention)

The aluminum chloride (0.045 g, 0.19 mmol) is added to a solution of fructose (2.0 g, 11.10 mmol) in DMSO (20 g). The feedstock/catalyst weight ratio is 111. The solvent/feedstock weight ratio is 10. The reaction medium is then stirred at 70° C. at 0.1 MPa for 6 h. The conversion of fructose into 5-HMF is monitored by regularly taking samples of an aliquot of solution which is instantly cooled to 0° C., redissolved in water and checked by gas chromatography, and by ion chromatography. The molar yield of 5-HMF after 6 h is 62%. The yield of unwanted humins is 30%.

Example 2

Fructose Conversion Using Lithium Chloride Alone in DMSO (Not in Accordance with the Invention)

The lithium chloride (0.008 g, 0.19 mmol) is added to a solution of fructose (2.0 g, 11.10 mmol) in DMSO (20 g). The feedstock/catalyst weight ratio is 111. The solvent/feedstock weight ratio is 10. The reaction medium is then stirred at 70° C. at 1 bar for 6 h. The conversion of fructose into 5-HMF is monitored by regularly taking samples of an aliquot of solution which is instantly cooled to 0° C., redissolved in water and checked by gas chromatography, and by ion chromatography and by size exclusion chromatography. The molar yield of 5-HMF after 6 h is 0%.

Example 3

Fructose Conversion Using Potassium Chloride Alone in DMSO (Not in Accordance with the Invention)

The potassium chloride (0.014 g, 0.19 mmol) is added to a solution of fructose (2.0 g, 11.10 mmol) in DMSO (20 g). The feedstock/catalyst weight ratio is 111. The solvent/feedstock weight ratio is 10. The reaction medium is then stirred at 70° C. at 0.1 MPa for 6 h. The conversion of fructose into 5-HMF is monitored by regularly taking samples of an aliquot of solution which is instantly cooled to 0° C., redissolved in water and checked by gas chromatography, and by ion chromatography. The molar yield of 5-HMF after 6 h is 0%.

Example 4

Fructose Conversion Using Aluminum Chloride and Lithium Chloride in DMSO (In Accordance with the Invention)

The aluminum chloride (0.045 g, 0.19 mmol) and the lithium chloride (0.008 g, 0.19 mmol) are added to a solution of fructose (2.0 g, 11.10 mmol) in DMSO (20 g). The feedstock/catalyst weight ratio is 111. The feedstock/chloride source weight ratio is 250. The solvent/feedstock weight ratio is 10. The reaction medium is then stirred at 70° C. at 0.1 MPa for 6 h. The conversion of fructose into 5-HMF is monitored by regularly taking samples of an aliquot of solution which is instantly cooled to 0° C., redissolved in water and checked by gas chromatography, and by ion chromatography. The molar yield of 5-HMF after 6 h is 79%. The yield of unwanted humins is 12%.

Example 5

Fructose Conversion Using Aluminum Chloride and Potassium Chloride in DMSO (In Accordance with the Invention)

The aluminum chloride (0.045 g, 0.19 mmol) and the potassium chloride (0.014 g, 0.19 mmol) are added to a solution of fructose (2.0 g, 11.10 mmol) in DMSO (20 g). The feedstock/catalyst weight ratio is 111. The feedstock/chloride source weight ratio is 140. The solvent/feedstock weight ratio is 10. The reaction medium is then stirred at 70° C. at 0.1 MPa for 6 h. The conversion of fructose into 5-HMF is monitored by regularly taking samples of an aliquot of solution which is instantly cooled to 0° C., redissolved in water and checked by gas chromatography, and by ion chromatography. The molar yield of 5-HMF after 6 h is 75%. The yield of unwanted humins is 15%.

Example 6

Fructose Conversion Using Aluminum Chloride and Choline Chloride in DMSO (In Accordance with the Invention)

The aluminum chloride (0.045 g, 0.19 mmol) and the choline chloride (0.027 g, 0.19 mmol) are added to a solution of fructose (2.0 g, 11.10 mmol) in DMSO (20 g). The feedstock/catalyst weight ratio is 111. The feedstock/chloride source weight ratio is 74. The solvent/feedstock weight ratio is 10. The reaction medium is then stirred at 70° C. at 0.1 MPa for 6 h. The conversion of fructose into 5-HMF is monitored by regularly taking samples of an aliquot of solution which is instantly cooled to 0° C., redissolved in water and checked by gas chromatography, and by ion chromatography. The molar yield of 5-HMF after 6 h is 78%. The yield of unwanted humins is 12%.

Example 7

Fructose Conversion Using Aluminum Chloride and Betaine Chloride in DMSO (In Accordance with the Invention)

The aluminum chloride (0.045 g, 0.19 mmol) and the choline chloride (0.029 g, 0.19 mmol) are added to a solution of fructose (2.0 g, 11.10 mmol) in DMSO (20 g). The feedstock/catalyst weight ratio is 111. The feedstock/chloride source weight ratio is 69. The solvent/feedstock weight ratio is 10. The reaction medium is then stirred at 70° C. at 0.1 MPa for 6 h. The conversion of fructose into 5-HMF is monitored by regularly taking samples of an aliquot of solution which is instantly cooled to 0° C., redissolved in water and checked by gas chromatography, and by ion chromatography. The molar yield of 5-HMF after 6 h is 80%. The yield of unwanted humins is 10%.

Example 8

Fructose Conversion Using Aluminum Chloride and Tetramethylammonium Chloride in DMSO (In Accordance with the Invention)

The aluminum chloride (0.045 g, 0.19 mmol) and the tetramethylammonium chloride (0.021 g, 0.19 mmol) are added to a solution of fructose (2.0 g, 11.10 mmol) in DMSO (20 g). The feedstock/catalyst weight ratio is 111. The feedstock/chloride source weight ratio is 95. The solvent/feedstock weight ratio is 10. The reaction medium is then stirred at 70° C. at 0.1 MPa for 6 h. The conversion of fructose into 5-HMF is monitored by regularly taking samples of an aliquot of solution which is instantly cooled to 0° C., redissolved in water and checked by gas chromatography, and by ion chromatography. The molar yield of 5-HMF after 6 h is 80%. The yield of unwanted humins is 10%.

Example 9

Fructose Conversion Using Aluminum Chloride and Lithium Bromide in DMSO (Not in Accordance with the Invention)

The aluminum chloride (0.045 g, 0.19 mmol) and the lithium chloride (0.016 g, 0.19 mmol) are added to a solution of fructose (2.0 g, 11.10 mmol) in DMSO (20 g). The feedstock/catalyst weight ratio is 111. The feedstock/bromide source weight ratio is 125. The solvent/feedstock weight ratio is 10. The reaction medium is then stirred at 70° C. at 0.1 MPa for 6 h. The conversion of fructose into 5-HMF is monitored by regularly taking samples of an aliquot of solution which is instantly cooled to 0° C., redissolved in water and checked by gas chromatography, and by ion chromatography. The molar yield of 5-HMF after 6 h is 63%. The yield of unwanted humins is 32%.

Example 10

Fructose Conversion Using Aluminum Chloride and Lithium Fluoride in DMSO (Not in Accordance with the Invention)

The aluminum chloride (0.045 g, 0.19 mmol) and the lithium fluoride (0.005 g, 0.19 mmol) are added to a solution of fructose (2.0 g, 11.10 mmol) in DMSO (20 g). The feedstock/catalyst weight ratio is 111. The feedstock/fluoride source weight ratio is 400. The solvent/feedstock weight ratio is 10. The reaction medium is then stirred at 70° C. at 0.1 MPa for 6 h. The conversion of fructose into 5-HMF is monitored by regularly taking samples of an aliquot of solution which is instantly cooled to 0° C., redissolved in water and checked by gas chromatography, and by ion chromatography. The molar yield of 5-HMF after 6 h is 0%.

TABLE 1

| Example | Feedstock | Dehydration catalyst | Chloride source | 5-HMF yield (%) | Unwanted products yield (%) |
|---|---|---|---|---|---|
| 1 (not in accordance with the invention) | Fructose | AlCl$_3$ | — | 63 | Humins 26 |
| 2 (not in accordance with the invention) | Fructose | — | LiCl | 0 | — |
| 3 (not in accordance with the invention) | Fructose | — | KCl | 0 | — |
| 4 (in accordance with the invention) | Fructose | AlCl$_3$ | LiCl | 77 | Humins 12 |
| 5 (in accordance with the invention) | Fructose | AlCl$_3$ | KCl | 74 | Humins 15 |
| 6 (in accordance with the invention) | Fructose | AlCl$_3$ | ChCl | 78 | Humins 12 |
| 7 (in accordance with the invention) | Fructose | AlCl$_3$ | BetCl | 81 | Humins 10 |
| 8 (in accordance with the invention) | Fructose | AlCl$_3$ | TMACl | 79 | Humins 10 |
| 9 (in accordance with the invention) | Fructose | AlCl$_3$ | LiBr | 61 | Humins 32 |
| 10 (in accordance with the invention) | Fructose | AlCl$_3$ | LiF | 0 | — |

The 5-HMF yield obtained by means of the process according to the invention is higher in the case of the combination of an inorganic dehydration catalyst such as AlCl$_3$ and a chloride source such as LiCl, KCl, ChCl, BetCl or TMACl in an aprotic polar solvent compared to the dehydration catalyst alone or the chloride source alone.

The formation of unwanted products such as humins is lower in the case of the association of an inorganic dehydration catalyst such as AlCl$_3$ and a chloride source such as LiCl, KCl, ChCl, BetCl or TMACl in an aprotic polar solvent according to the invention compared to the dehydration catalyst alone.

The 5-HMF yield is higher in the case of the combination of an inorganic dehydration catalyst such as AlCl$_3$ and a chloride source such as LiCl, KCl, ChCl, BetCl or TMACl in an aprotic polar solvent according to the invention compared to the combination of a dehydration catalyst in combination with a bromide source LiBr or a fluoride source LiF.

It therefore unexpectedly appears that it is clearly advantageous to use dehydration catalysts in combination with a chloride source in an aprotic polar solvent according to the invention for the conversion of sugars into 5-HMF.

The invention claimed is:

1. A process for converting a feedstock comprising at least one sugar into 5-hydroxymethylfurfural, wherein said feedstock is brought into contact with at least one inorganic dehydration catalyst and at least one chloride source of formula (IIIb)

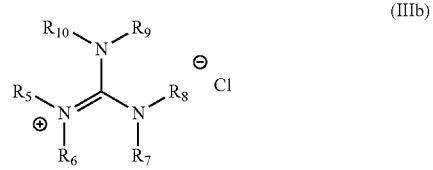

wherein the groups $R_5$ to $R_{10}$, which may be identical or different, are independently alkyl groups with 1 to 20 carbon atoms, or aryl groups with 5 to 20 carbon atoms, in the presence of at least one aprotic polar solvent, at a temperature of 30° C. to 200° C. and a pressure of 0.1 to 10 MPa.

2. The process as claimed in claim 1, wherein the feedstock comprises oligosaccharides or monosaccharides, alone or as a mixture.

3. The process as claimed in claim 1, wherein the feedstock is sucrose, lactose, maltose, isomaltose, inulobiose, melibiose, gentiobiose, trehalose, cellobiose, cellotriose, cellotetraose or oligosaccharides resulting from the hydrolysis of said polysaccharides resulting from the hydrolysis of starch, inulin, cellulose or hemicellulose, alone or as a mixture.

4. The process as claimed in claim 1, wherein the dehydration catalyst(s) are independently homogeneous inorganic Brønsted acids or homogeneous or heterogeneous inorganic Lewis acids.

5. The process as claimed in claim 4, wherein the inorganic Brønsted acid(s) are HF, HCl, HBr, HI, $H_2SO_3$, $H_2SO_4$, $H_3PO_2$, $H_3PO_4$, $HNO_2$, $HNO_3$, $H_2WO_4$, $H_4SiW_{12}O_{40}$, $H_3PW_{12}O_{40}$, $(NH_4)_6(W_{12}O_{40}).xH_2O$, $H_4SiMo_{12}O_{40}$, $H_3PMo_{12}O_{40}$, $(NH_4)_6Mo_7O_{24}.xH_2O$, $H_2MoO_4$, $HReO_4$, $H_2CrO_4$, $H_2SnO_3$, $H_4SiO_4$, $H_3BO_3$, $HClO_4$, $HBF_4$, $HSbF_5$, $HPF_6$, $H_2FO_3P$, $ClSO_3H$, $FSO_3H$, $HN(SO_2F)_2$ or $HIO_3$.

6. The process as claimed in claim 4, wherein the homogeneous inorganic Lewis acid(s) are compounds of formula (II) $M_oX_p$, which are optionally solvated, wherein M is an atom from groups 3 to 16 of the periodic table, lanthanides included, o is an integer 1 to 10, p is an integer 1 to 10, and X is an optionally substituted hydroxide, halide, nitrate, carboxylate, halocarboxylate, acetylacetonate, alkoxide, or phenolate anion, or a sulfate, alkyl sulfate, phosphate, alkyl phosphate, halosulfonate, alkyl sulfonate, perhaloalkyl sulfonate, bis(perhaloalkylsulfonyl)amide, or arenesulfonate, which are optionally substituted with halogen or haloalkyl groups.

7. A process for converting a feedstock comprising at least one sugar into 5-hydroxymethylfurfural, wherein said feedstock is brought into contact with at least one inorganic dehydration catalyst and at least one chloride source of formula (IIIc)

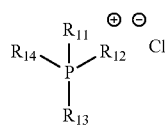

(IIIc)

wherein $R_{11}$ to $R_{14}$, which may be identical or different, are independently alkyl groups, aryl groups, phosphazene groups of formula

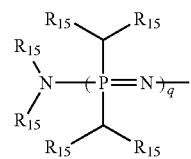

wherein $R_{15}$ is an alkyl group with 1 to 10 carbon atoms, and q an integer 0 to 10, in the presence of at least one aprotic polar solvent, at a temperature of 30° C. to 200° C. and a pressure of 0.1 to 10 MPa.

8. The process as claimed in claim 1, wherein the aprotic polar solvent(s) are aprotic polar solvents of which the dipole moment expressed in Debye (D) is greater than or equal to 2.00.

9. The process as claimed in claim 1, wherein at least one aprotic polar solvent, alone or as a mixture, is pyridine, butan-2-one, acetone, acetic anhydride, N,N,N',N'-tetramethylurea, benzonitrile, acetonitrile, methyl ethyl ketone, propionitrile, hexamethylphosphoramide, nitrobenzene, nitromethane, N,N-dimethylformamide, N,N-dimethylacetamide, sulfolane, N-methylpyrrolidone, dimethyl sulfoxide, propylene carbonate or γ-valerolactone.

10. The process as claimed in claim 1, wherein the feedstock is introduced into the process in an amount corresponding to a solvent/feedstock weight ratio of 0.1 to 200.

11. The process as claimed in claim 1, wherein the dehydration catalyst(s) are introduced into the reaction chamber in an amount corresponding to a feedstock/catalyst(s) weight ratio of 1 to 1000.

12. The process as claimed in claim 1, wherein the chloride source(s) are introduced into the reaction chamber in an amount corresponding to a feedstock/chloride source(s) weight ratio of 1 to 1000.

13. The process as claimed in claim 7, wherein the feedstock comprises oligosaccharides or monosaccharides, alone or as a mixture.

14. The process as claimed in claim 7, wherein the feedstock is sucrose, lactose, maltose, isomaltose, inulobiose, melibiose, gentiobiose, trehalose, cellobiose, cellotriose, cellotetraose or oligosaccharides resulting from the hydrolysis of said polysaccharides resulting from the hydrolysis of starch, inulin, cellulose or hemicellulose, alone or as a mixture.

15. The process as claimed in claim 7, wherein the dehydration catalyst(s) are independently homogeneous inorganic Brønsted acids or homogeneous or heterogeneous inorganic Lewis acids.

16. The process as claimed in claim 15, wherein the inorganic Brønsted acid(s) are HF, HCl, H Br, HI, $H_2SO_3$, $H_2SO_4$, $H_3PO_2$, $H_3PO_4$, $HNO_2$, $HNO_3$, $H_2WO_4$, $H_4SiW_{12}O_{40}$, $H_3PW_{12}O_{40}$, $(NH_4)_6(W_{12}O_{40}).xH_2O$, $H_4SiMo_{12}O_{40}$, $H_3PMo_{12}O_{40}$, $(NH_4)_6Mo_7O_{24}.xH_2O$, $H_2MoO_4$, $HReO_4$, $H_2CrO_4$, $H_2SnO_3$, $H_4SiO_4$, $H_3BO_3$, $HClO_4$, $HBF_4$, $HSbF_5$, $HPF_6$, $H_2FO_3P$, $ClSO_3H$, $FSO_3H$, $HN(SO_2F)_2$ or $HIO_3$.

17. The process as claimed in claim 15, wherein the homogeneous inorganic Lewis acid(s) are compounds of formula (II) $M_oX_p$, which is optionally solvated, wherein M is an atom from groups 3 to 16 of the periodic table, lanthanides included, o is an integer 1 to 10, p is an integer 1 to 10, and X is an optionally substituted hydroxide, halide, nitrate, carboxylate, halocarboxylate, acetylacetonate, alkoxide, or phenolate anion, or a sulfate, alkyl sulfate, phosphate, alkyl phosphate, halosulfonate, alkyl sulfonate, perhaloalkyl sulfonate, bis(perhaloalkylsulfonyl)amide, or arenesulfonate, which are optionally substituted with halogen or haloalkyl groups.

18. The process according to claim 7, wherein the aprotic polar solvent(s) are aprotic polar solvents of which the dipole moment expressed in Debye (D) is greater than or equal to 2.00.

19. The process as claimed in claim 7, wherein the dehydration catalyst(s) are introduced into the reaction chamber in an amount corresponding to a feedstock/catalyst(s) weight ratio of 1 to 1000.

20. The process as claimed in claim 7, wherein the chloride source(s) are introduced into the reaction chamber in an amount corresponding to a feedstock/chloride source(s) weight ratio of 1 to 1000.

* * * * *